US00PP31403P2

(12) United States Plant Patent
Pierron-Darbonne

(10) Patent No.: US PP31,403 P2
(45) Date of Patent: Jan. 28, 2020

(54) BLUEBERRY PLANT NAMED 'PLABLUE 1542'

(50) Latin Name: ***Vaccinium corymbosum* L.**
Varietal Denomination: Plablue 1542

(71) Applicant: Plantas de Navarra, S.A. Sociedad Unipersonal, Navarra (ES)

(72) Inventor: Alexandre Pierron-Darbonne, Pamplona (ES)

(73) Assignee: Plantas de Navarra, S.A. Sociedad Unipersonal (ES)

( * ) Notice: Subject to any disclaimer, the term of this patent is extended or adjusted under 35 U.S.C. 154(b) by 0 days.

(21) Appl. No.: 16/501,260

(22) Filed: Mar. 13, 2019

(30) Foreign Application Priority Data

Aug. 9, 2018 (QZ) ..... PBR 2018/2072

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

*Primary Examiner* — Susan McCormick Ewoldt
*Assistant Examiner* — Karen M Redden
(74) *Attorney, Agent, or Firm* — Knobbe, Martens, Olson & Bear, LLP

(57) ABSTRACT

Described is a new and distinct blueberry variety with varietal denomination 'Plablue 1542', characterized by a combination of traits which include, an upright plant growth habit, and very abundant production of large fruit-size, oblate shaped and very firm fruit. 'Plablue 1542' is a self-fertile variety.

16 Drawing Sheets

Botanical classification: *Vaccinium corymbosum* L.

Variety denomination: The new plant has the varietal denomination 'Plablue 1542'.

CROSS-REFERENCE TO RELATED APPLICATIONS

This application claims the benefit of European Community Plant Variety Office Application No. 2018/2072, for a blueberry variety named 'Plablue 1542,' filed on Aug. 09, 2018, the entirety of which is incorporated by reference herein.

BACKGROUND

Disclosed herein is a new and distinct southern highbush blueberry variety (*Vaccinium corymbosum* L.). The varietal denomination of the new variety is 'Plablue 1542.' The new variety of blueberry was created in a breeding program by crossing two parents; in particular, by crossing as seed parent an undistributed blueberry parent designated 14.027.001 (unpatented) and as pollen parent an undistributed blueberry parent designated 14.049.001 (unpatented). Female and male are selections from breeder's program of the applicant. Both parental varieties are proprietary and have not been commercialized.

The new variety was grown and asexually propagated by softwood cuttings in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

The growing period in Huelva, Spain, where the observations on primocane production were made, is between about November 20 and June 22 of the following year.

SUMMARY

The present invention relates to a new and distinct southern highbush blueberry variety. The varietal denomination of the new variety is 'Plablue 1542', that produces and maintains a weak vigorous plant with consistent fruit production from beginning February through middle June. Among the characteristics which appear to distinguish the new variety from other varieties are a combination of traits which include an upright plant growth habit, and very abundant production of large fruit-size, oblate shaped and very firm fruit.

The new blueberry plant variety 'Plablue 1542' has not been observed under all possible environmental conditions. The phenotype may vary somewhat with variations in environmental and cultural practices such as temperature and light intensity without, however, any variance in genotype.

COMPARISON TO THE PARENTS

The new variety is distinguished from its parents by the following characteristics which are different than the seed parent designated '14.027.001' (unpatented) and the pollen parent designated '14.049.001' (unpatented).

Size of corolla tube in the flower of seed parent '14.027.001' (unpatented) is higher than in the flower of 'Plablue 1542'.

Seed parent '14.027.001' (unpatented) shows a medium fruit size, whereas 'Plablue 1542' shows a large fruit size.

Seed parent '14.027.001' (unpatented) shows a rounded fruit shape, whereas 'Plablue 1542' shows an oblated fruit shape.

Leaf of pollen parent '14.049.001' (unpatented) shows a margin entire, whereas leaf of 'Plablue 1542' shows a margin serrate.

Pollen parent '14.049.001' (unpatented) shows a short length of internode on one-year-old shoot, whereas 'Plablue 1542' shows a long length.

COMPARISON TO CLOSEST VARIETY

The new variety is closest to the variety 'Biloxi' (unpatented), but is distinguished therefrom by the following characteristics which are different than 'Biloxi'.

Plant of 'Biloxi' (unpatented) exhibits a semi upright grow habit, whereas the plant of 'Plablue 1542' exhibits an upright growth habit.

Length of the leaf of 'Biloxi' (unpatented) is shorter than length of the leaf of 'Plablue 1542' and width of the leaf of 'Biloxi' (unpatented) is narrower than the leaf of 'Plablue 1542'.

Length of inflorescence of 'Biloxi' (unpatented) is shorter than length of inflorescence of 'Plablue 1542'.

Density of fruit cluster of 'Biloxi' (unpatented) is higher than density of fruit cluster of 'Plablue 1542'.

Fruit size of 'Biloxi' (unpatented) is medium and shows a soft firmness, whereas in 'Plablue 1542' fruit size is large and is very firm.

Time of beginning of flowering on one-year-old shoot of 'Biloxi' (unpatented) is less early than in 'Plablue 1542'.

Time of beginning of fruit ripening on one-year-old shoot of 'Biloxi' (unpatented) is less early than in 'Plablue 1542'.

Differences in grow habit of 'Plablue 1542' (designated 15.09.003) and 'Biloxi' (unpatented) are shown in FIG. 1 and FIG. 13. Differences in length and width of leaf of 'Plablue 1542' (designated 15.09.003) and 'Biloxi' (unpatented) are shown in FIG. 3 and FIG. 14. Differences in density of fruit cluster of 'Plablue 1542' (designated 15.09.003) and 'Biloxi' (unpatented) are shown in FIG. 2, FIG. 6 and FIG. 15. Differences in fruit size of 'Plablue 1542' (designated 15.09.003) and 'Biloxi' (unpatented) are shown in FIG. 9 and FIG. 16. These differences are maintained during the harvest season.

BRIEF DESCRIPTION OF THE ILLUSTRATIONS

The accompanying photographs show typical specimens of the new variety, designated 15.09.003 in the illustrations, including fruit, foliage and flower, in color as nearly true as it is reasonably possible to make in color illustrations of this character.

The plants depicted in the drawings were planted October 14 in the farm of La Mogalla in Cartaya (Huelva), Spain, about 7° W, 37° N, 45 feet elevation.

Drawings/photographs were taken in April (about April 4 and April 12): minimum temperate about 7° to 9° Centigrade, maximum temperate about 18 to 22° Centigrade.

FIG. 1 and FIG. 2 show several plants of the new variety (designated 15.09.003) which exhibit a upright habit plant with several clusters of violet-blue color fruit (RHS Violet-Blue group color near 97 D to 97 C) with wax and oblated shape fruits.

FIG. 3 and FIG. 4 show the upper side and the underside, respectively, of a complete leave of the new variety (designated 15.09.003). In it, we can see that the leaf color of upper side of the new variety (designated 15.09.003) is a green color (RHS Green group near 143 B to 143 A) and the leaf color of underside of the new variety (designated 15.09.003) is a yellow-green color (RHS Yellow-Green group color near 144 B to 144 A).

Figure 1:
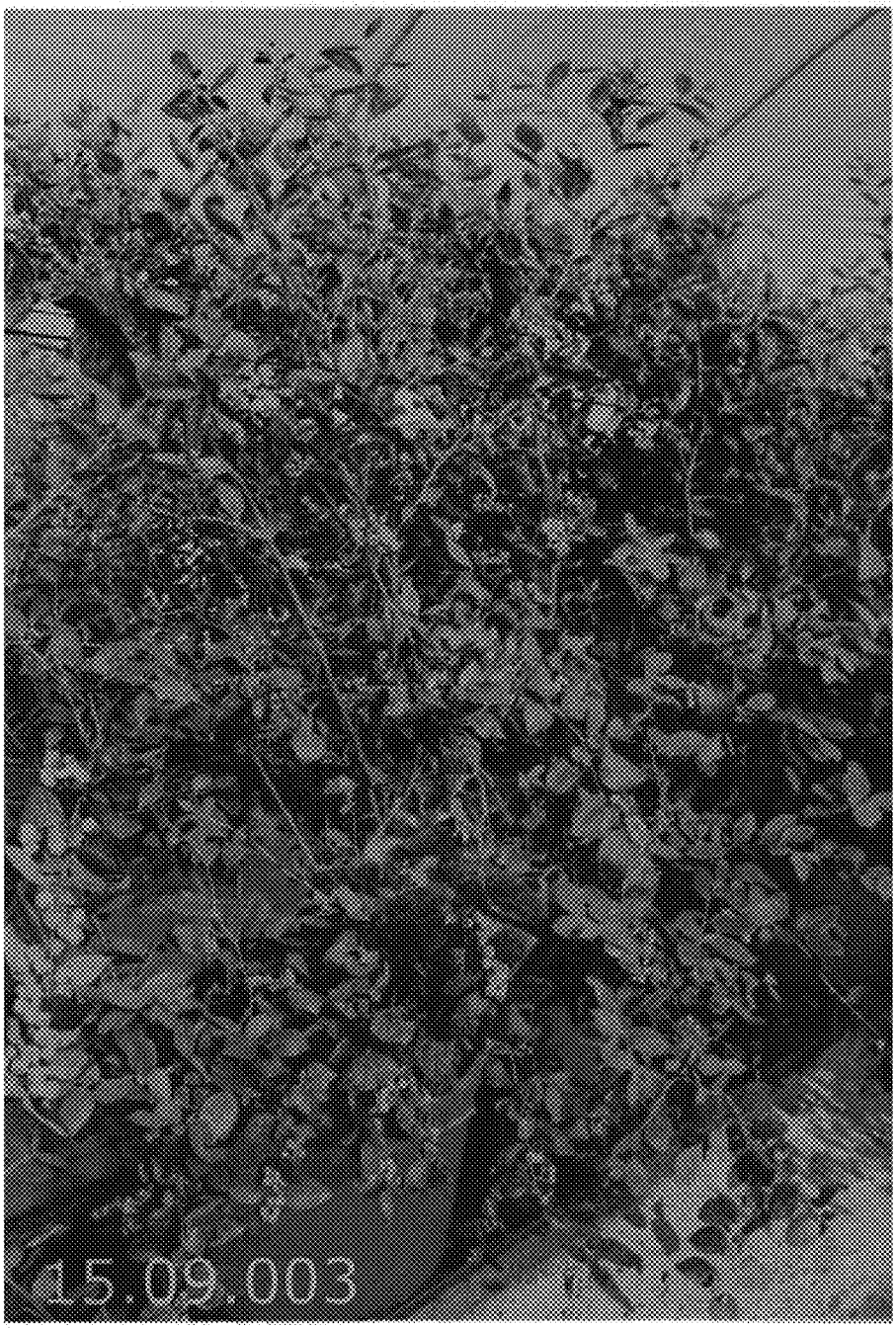
Figure 2:
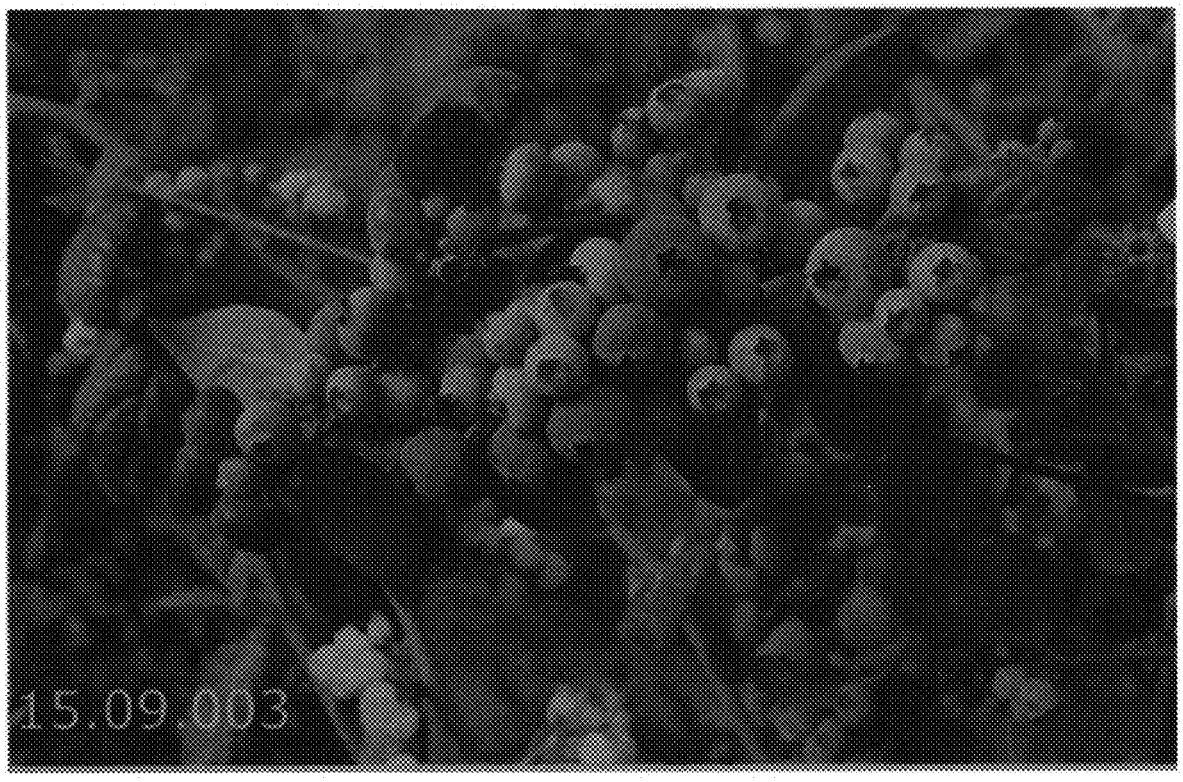
Figure 3:
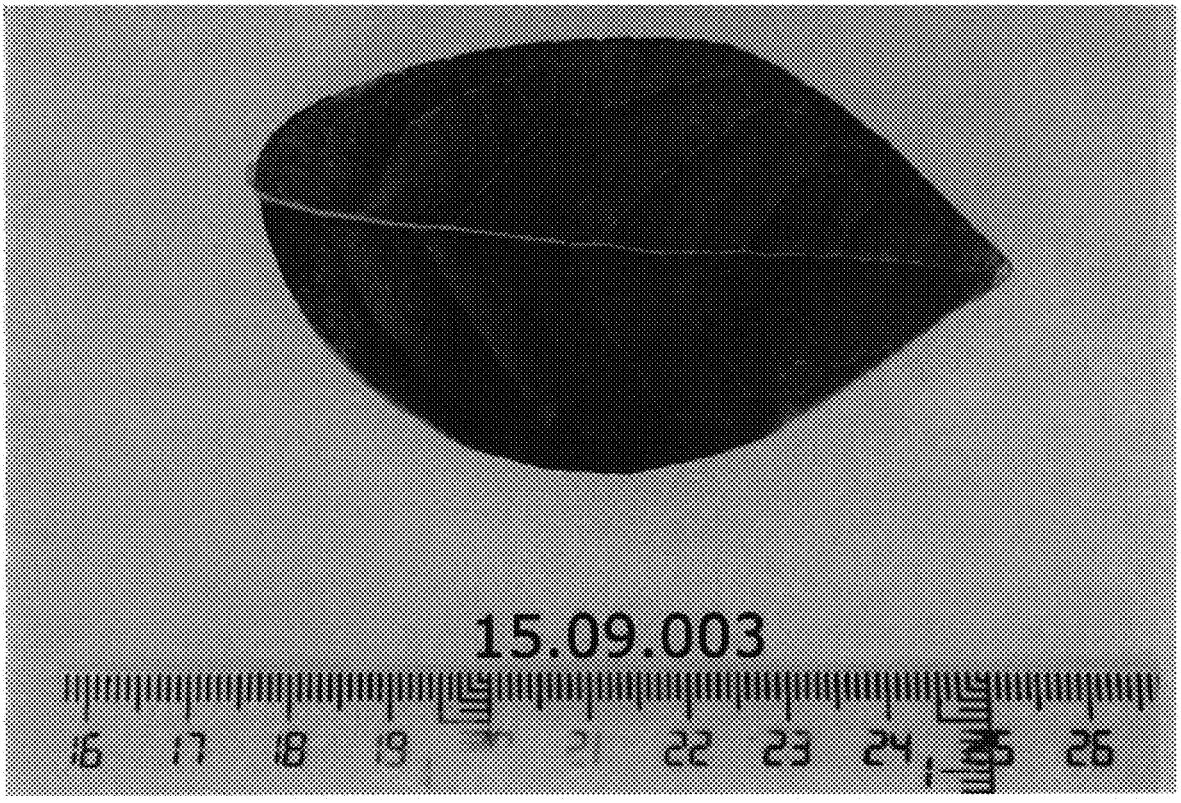
Figure 4:
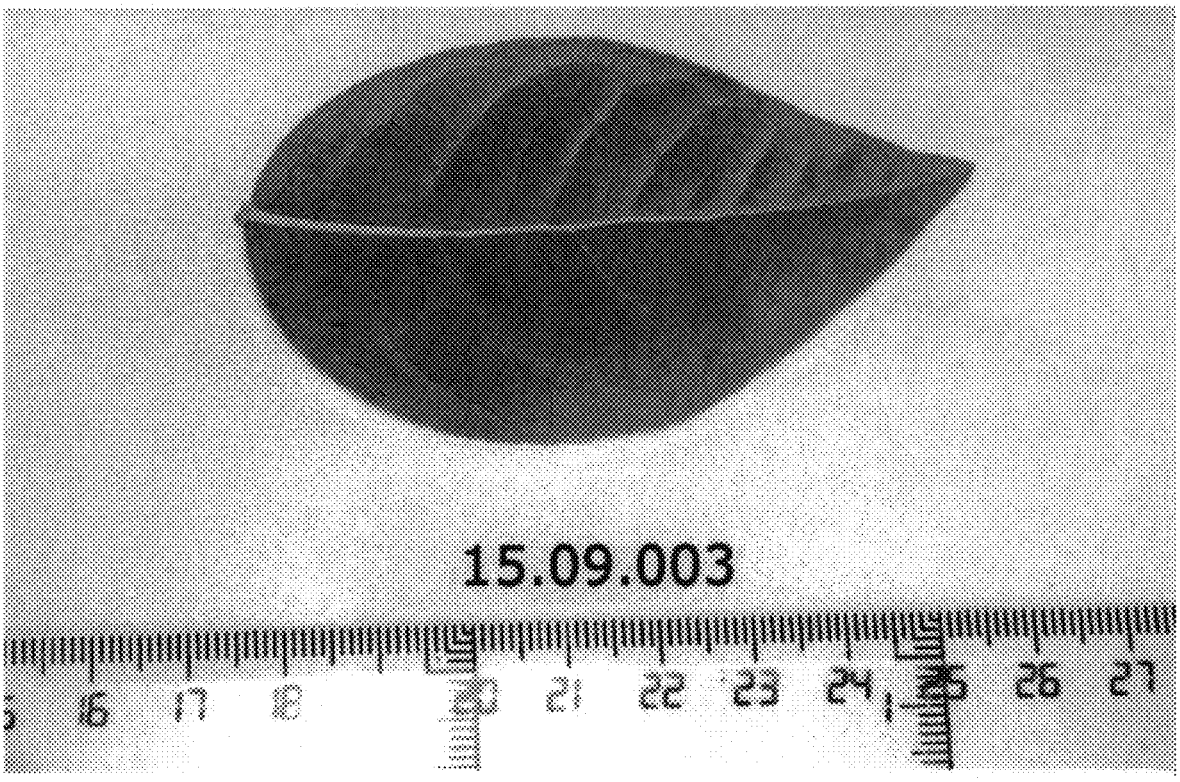
Figure 5:
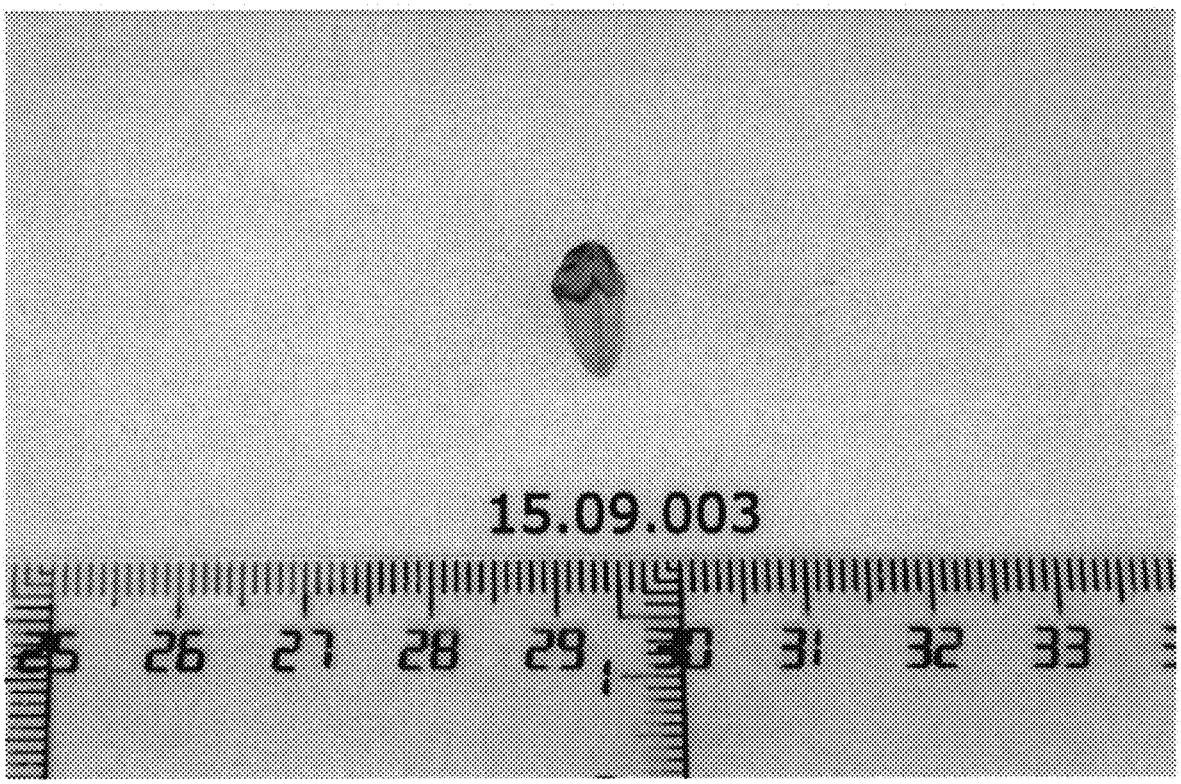
FIG. 5 shows an immature flower of the new variety (designated 15.09.003). In it, we can see the immature flower has a red color (RHS Red group color near 54 C to 54 B).
Figure 6:
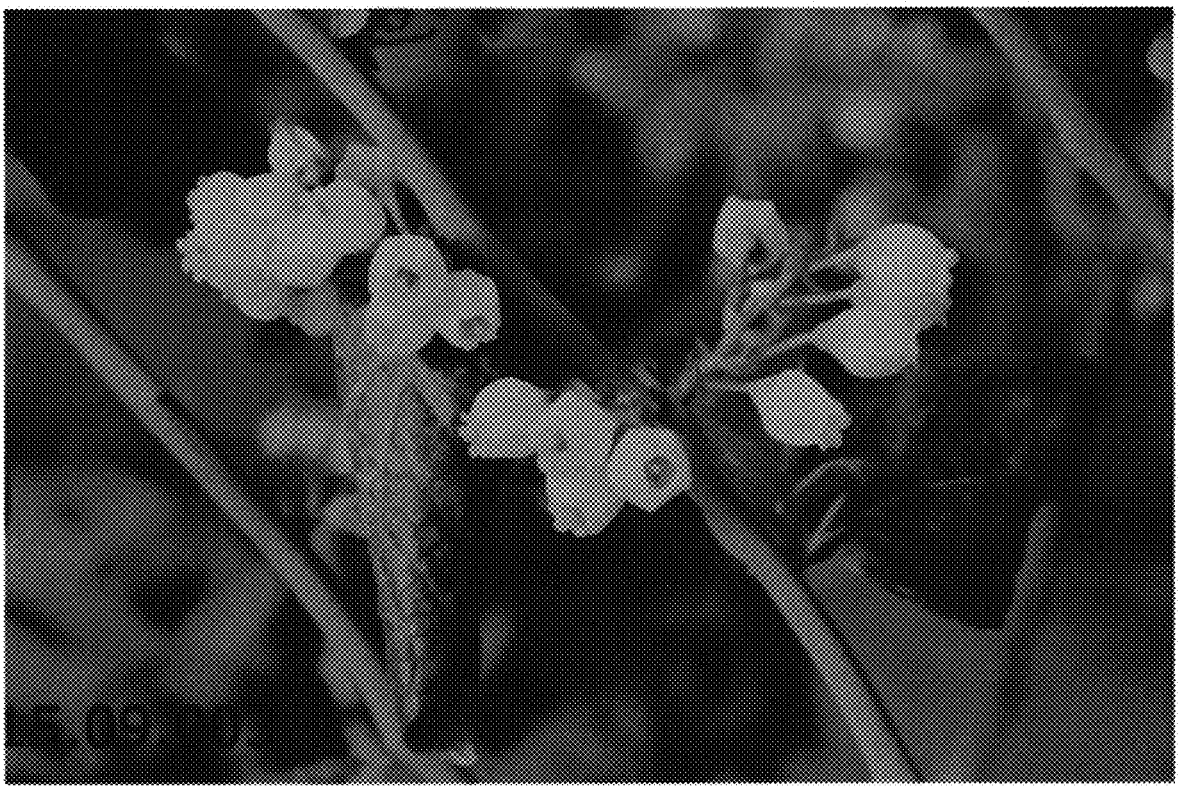
FIG. 6 shows a typical cluster with flowers of the new variety (designated 15.09.003).
Figure 7:
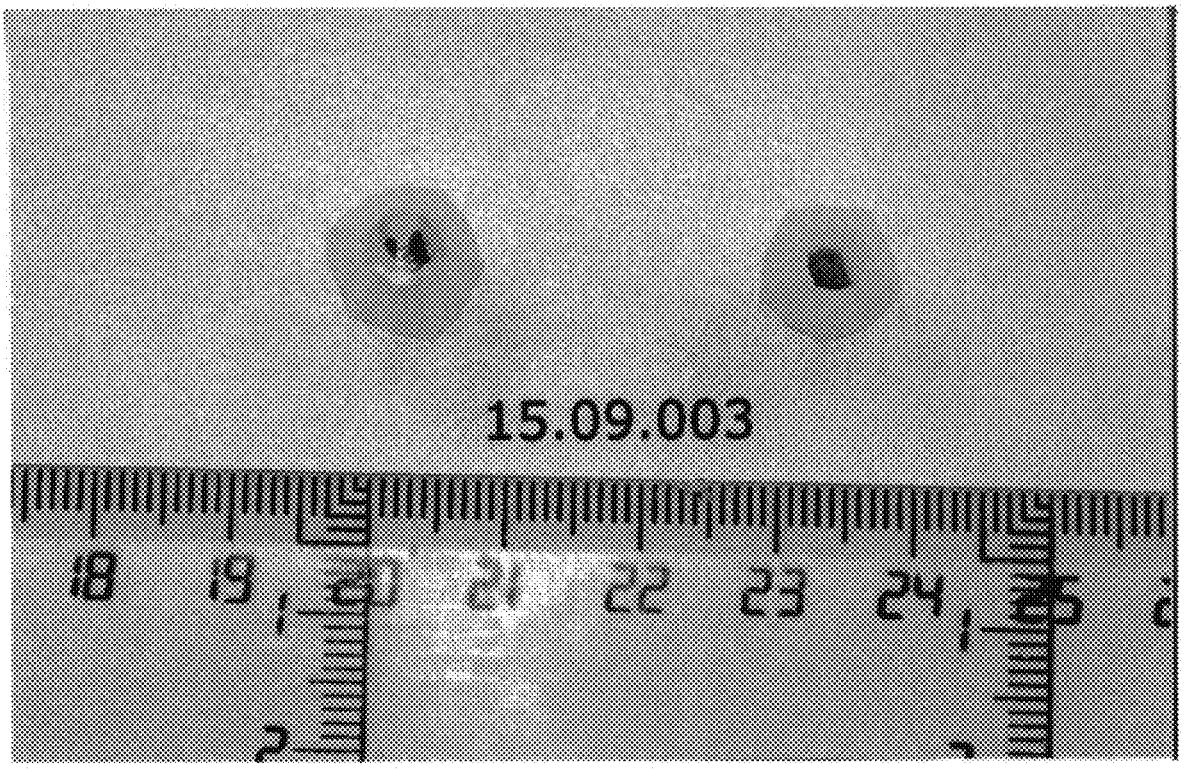

FIG. 7 shows corolla of the new variety (designated 15.09.003) with white color (RHS White group color near 155 B to 155 A) and greyed-orange color anthers (RHS Greyed-Orange group color near 165 B to 165 A).

Figure 8:
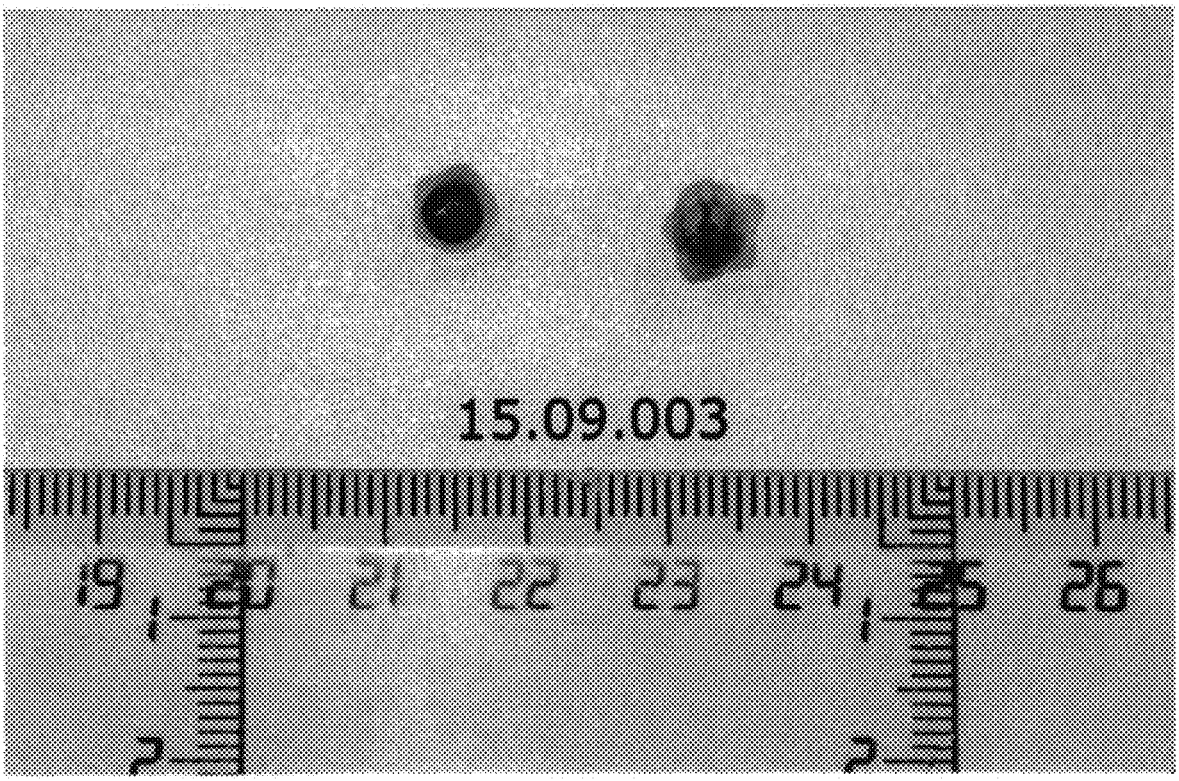

FIG. 8 shows typical sepals of the new variety (designated 15.09.003) with yellow-green color (RHS Yellow-Green group color near 144 D to 144 C).

Figure 9:
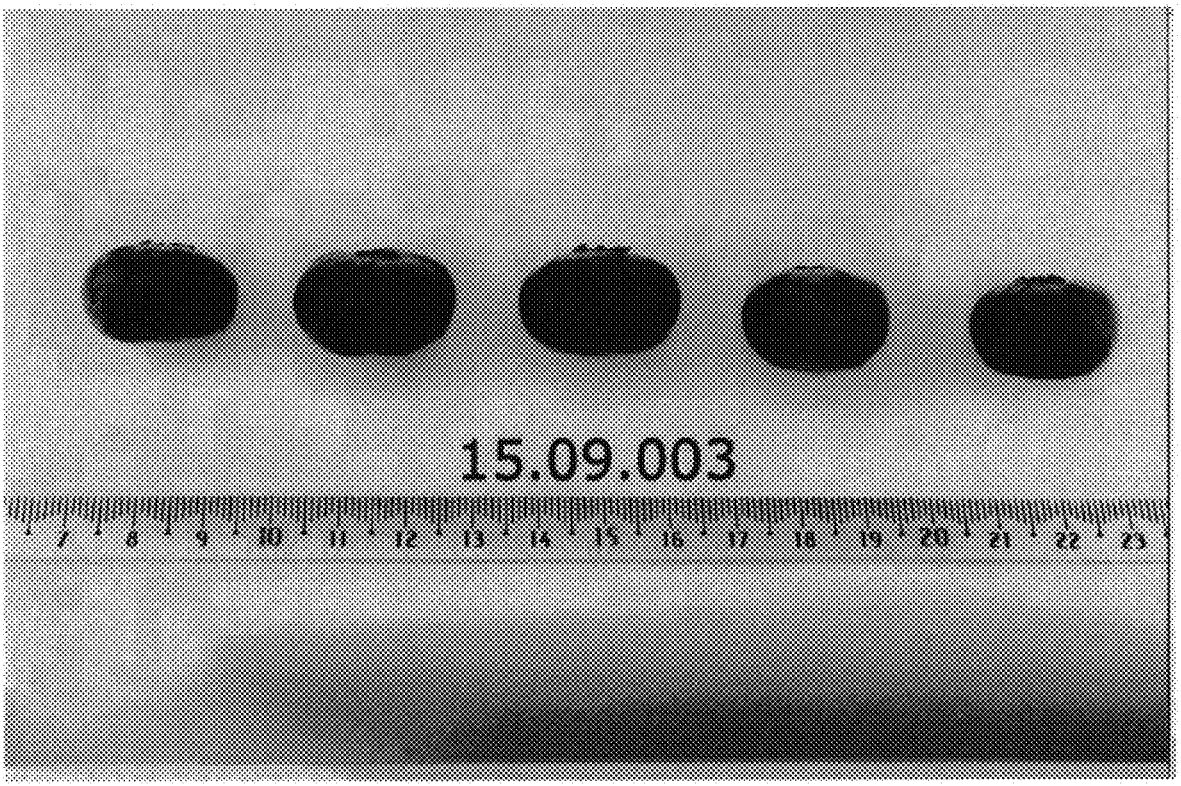
Figure 10:
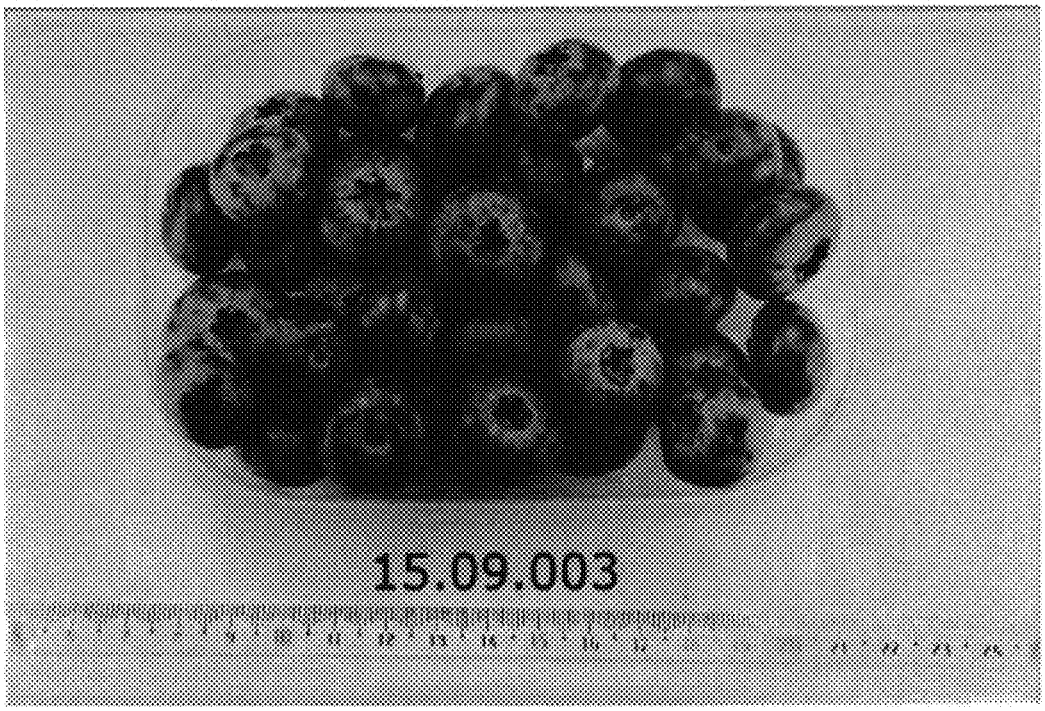

FIG. 9 and FIG. 10 show typical fruits of the new variety (designated 15.09.003) with oblate shape and violet-blue color with wax (RHS Violet-Blue group color near 97 D to 97 C).

Figure 11:
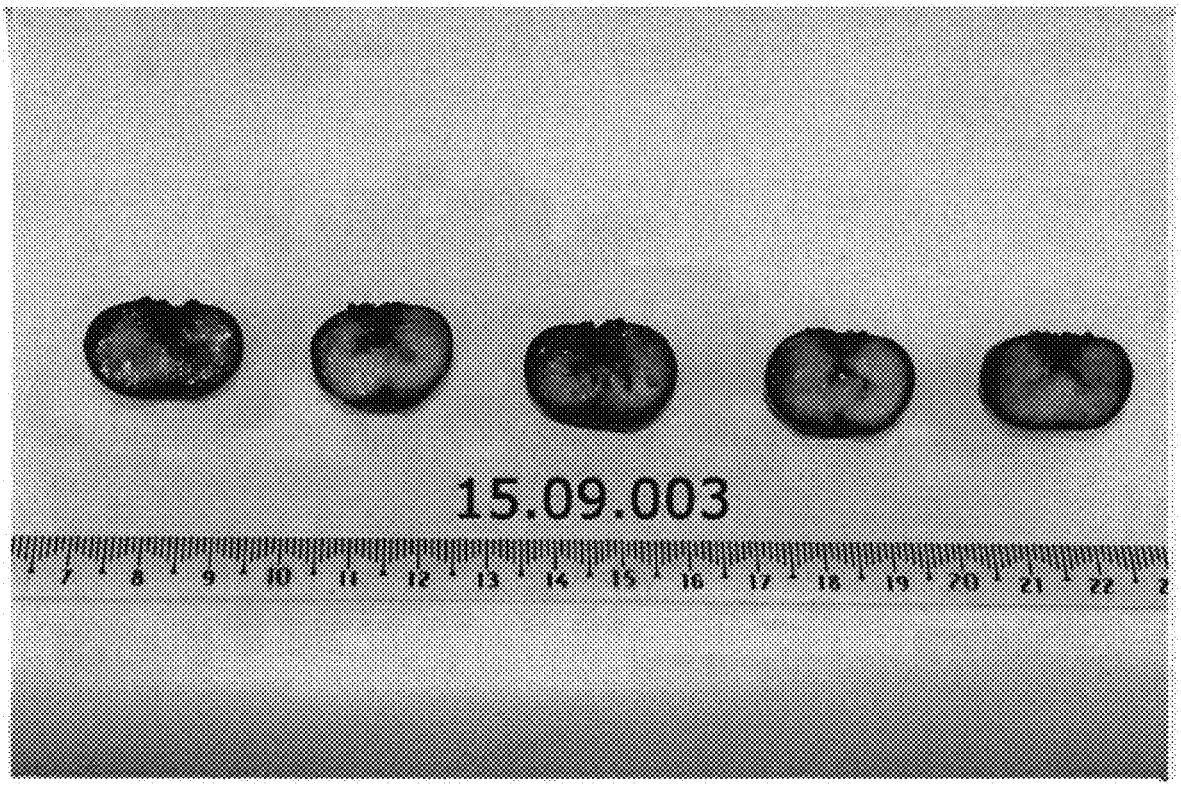

FIG. 11 shows typical sliced fruits of the new variety (designated 15.09.003) with yellow-green flesh color (RHS Yellow-Green group color near 149 D to 149 C).

Figure 12:
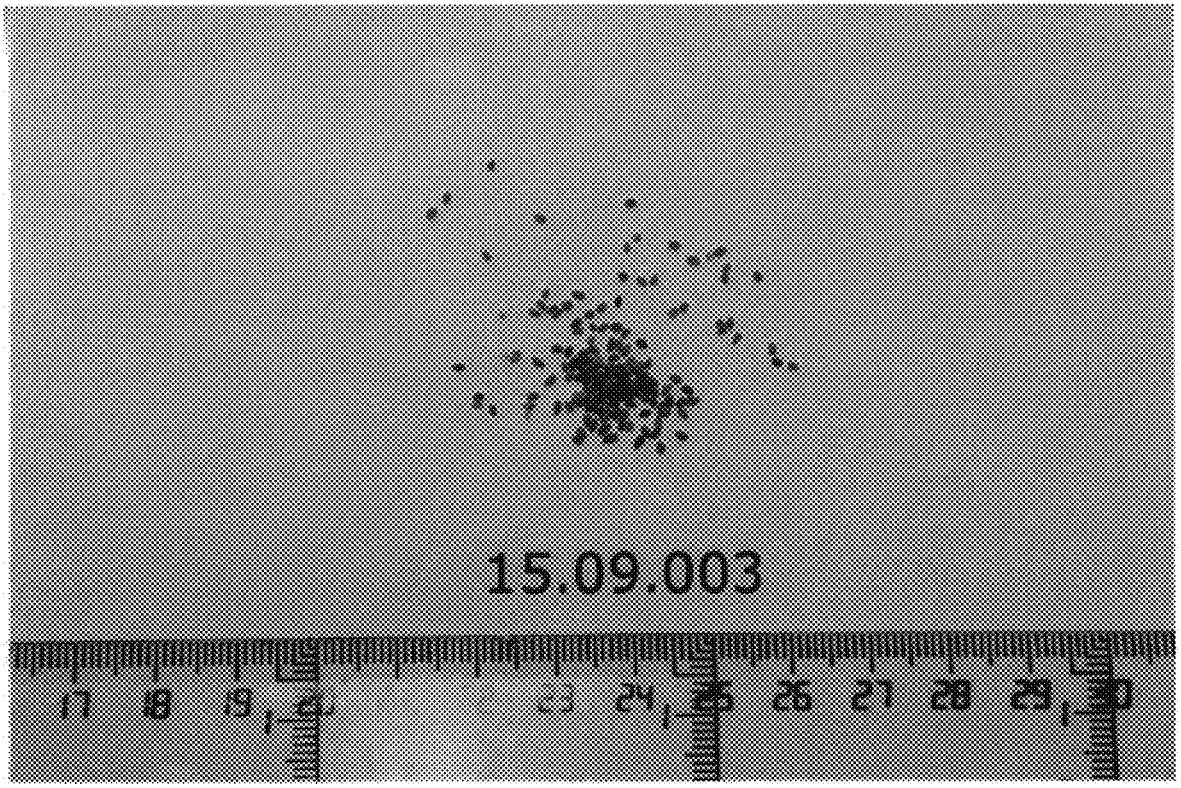

FIG. 12 shows typical seeds of the new variety (designated 15.07.018) with greyed-orange color (RHS Greyed-Orange group color near 165 C to 165 B).

Figure 13:
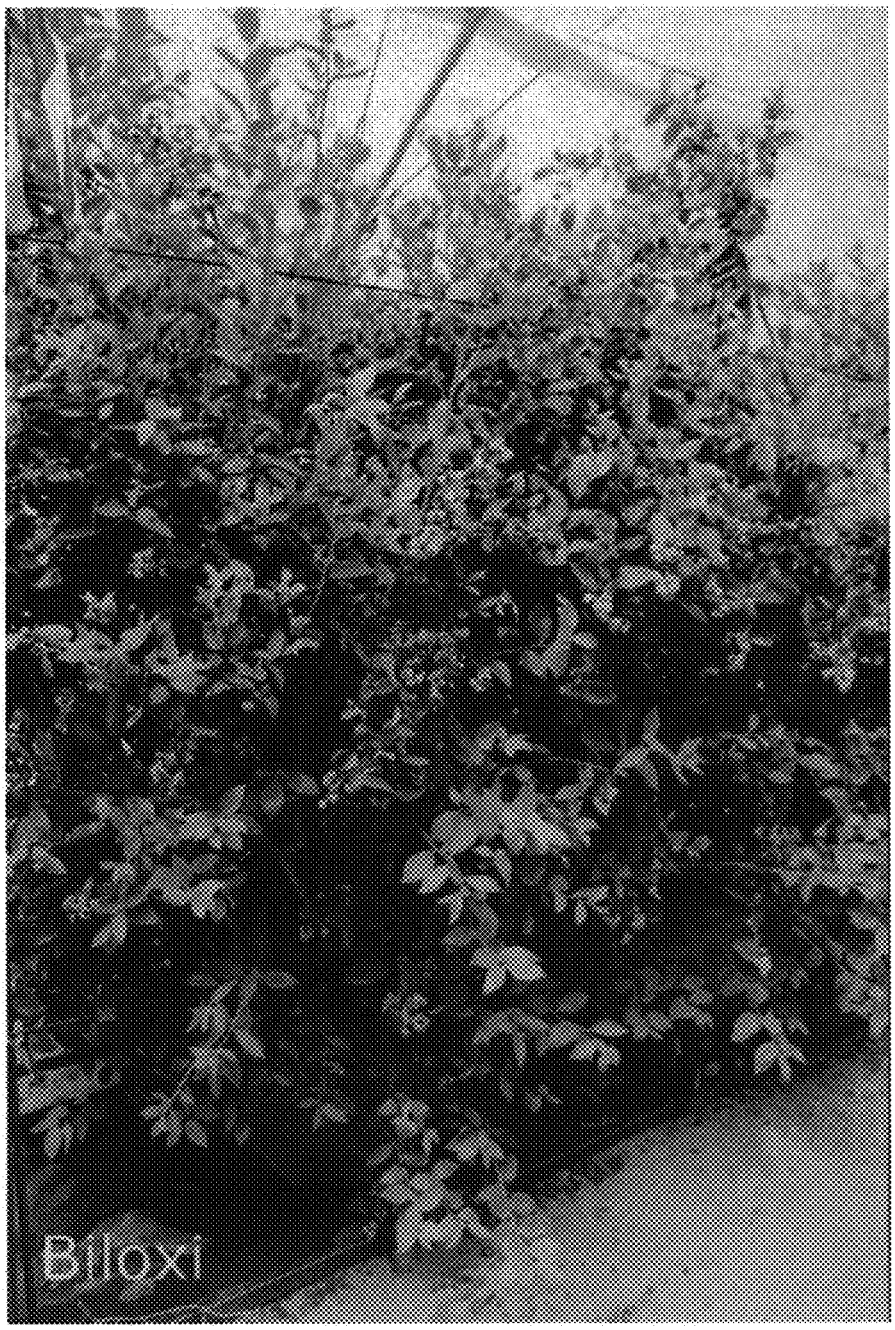

FIG. 13 shows several plants of the blueberry variety 'Biloxi' (unpatented) which exhibits a semi upright habit.

Figure 14:
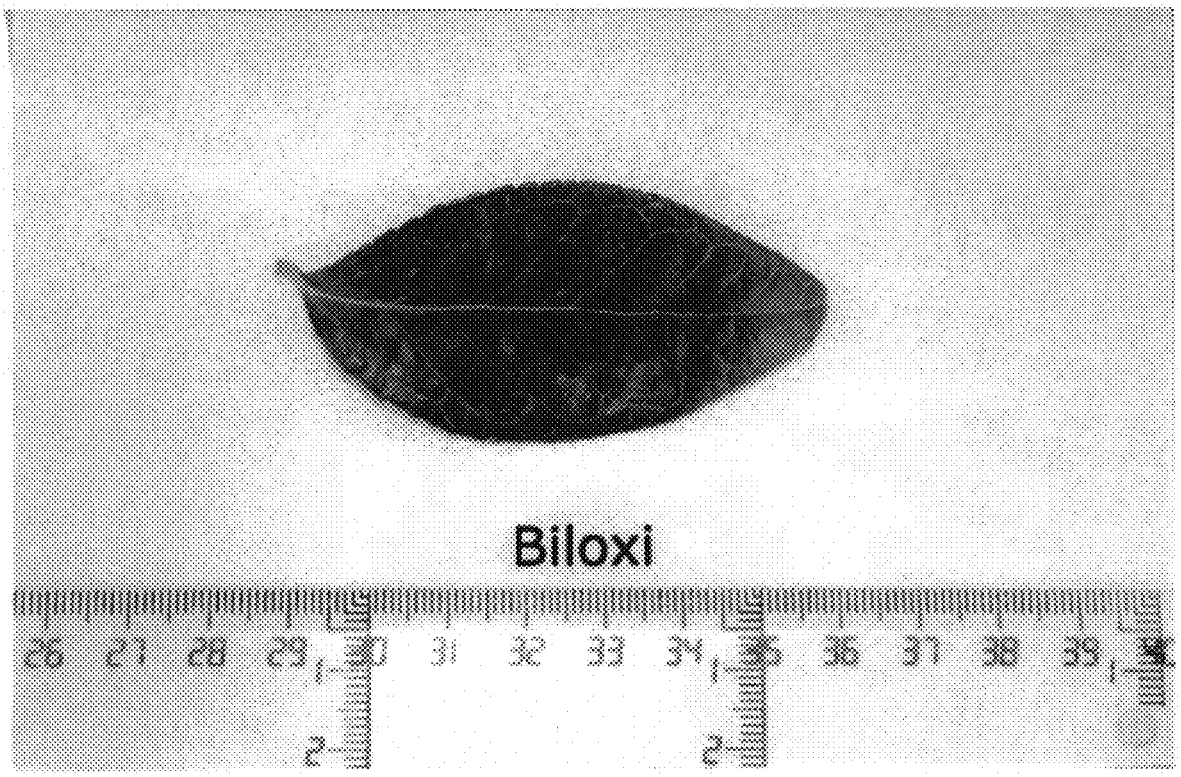

FIG. 14 shows the leaf of blueberry variety 'Biloxi' (unpatented) shorter and narrower than the leaf of the new variety (designated 15.09.003).

Figure 15:
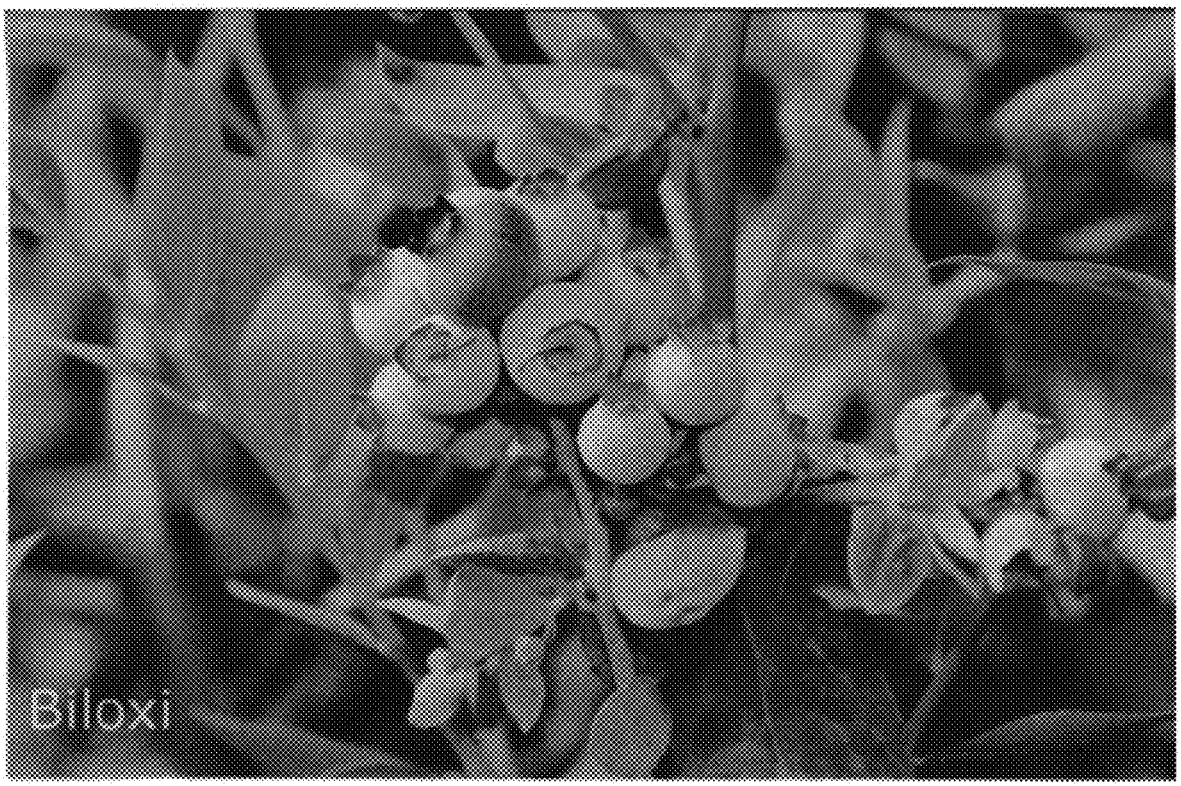

FIG. 15 shows the density of fruit cluster of 'Biloxi' (unpatented) which is higher than density of fruit cluster of the new variety (designated 15.09.003).

Figure 16:
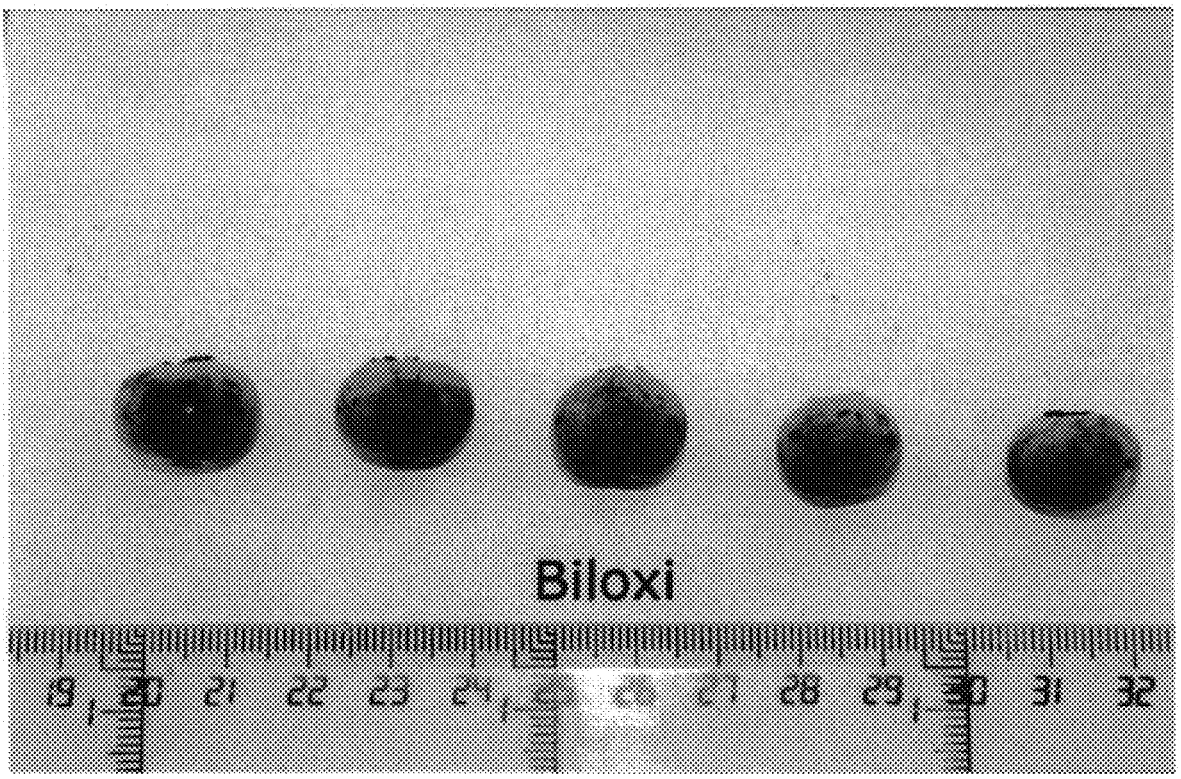

FIG. 16 shows fruits of blueberry variety 'Biloxi' (unpatented) which exhibits a fruit size smaller than the fruit of the new variety (designated 15.09.003).

DESCRIPTION OF THE NEW VARIETY

The following detailed description of the new variety is based upon observations taken of plants and fruits grown "underglass", i.e. undertunnel, in the farm of La Mogalla in Cartaya (Huelva), Spain, 7° W., 37° N., 45 feet elevation.

The following description is in accordance with UPOV terminology and the color teminology herein is in accordance with The Royal Horticultural Society Colour Chart (R.H.S.C.C.), 3$^{rd}$ edition published in 1995. The color descriptions and other phenotypical descriptions may deviate from the stated values and descriptions depending upon variation in environmental, seasonal, climatic and cultural conditions.

PROPAGATION

The new variety is principally propagated by softwood cuttings. Although propagation by softwood cuttings is presently preferred, other know methods of propagating blueberry plants may be used.

Blueberry root and develop well after transplanting.

GENERAL

'Plablue 1542' is propagated by softwood cuttings. It is a variety with fruit production from beginning February through middle June. It is a self-fertile variety. It produces large quantities of pollen throughout the seasons and pollination is good.

Production: Plants described are from a high elevation nursery in Segovia, Spain, 3° 59'W., 41° 22'N., 2742 feet elevation.

Trials pursued in Cartaya (Huelva), Spain.

Date of planting: 14th October.

Number of repetitions: 2

Plants per repetition: 50

TABLE 1

Table 1 shows the accumulated production of fruit (g/plant) of the new variety 'Plablue 1542' when compared to its closest varieties 'Biloxi' and 'Star' (U.S. Plant Pat. No. 10,675).

| Variety | February 27 | March 31 | April 30 | June 22 |
|---|---|---|---|---|
| Plablue 1542 | 711.00 | 2099.00 | 3127.00 | 5290.00 |
| Biloxi | 191.67 | 477.33 | 905.33 | 2850.00 |
| Star | 0.00 | 757.67 | 1781.73. | 1803.10 |

TABLE 2

Table 2 shows the weight (g/fruit) at three dates of the new variety 'Plablue 1542' when compared to its closest varieties 'Biloxi' and 'Star'.

| Variety | March 31 | April 30 | June 22 |
|---|---|---|---|
| Plablue 1542 | 22.00 | 22.00 | 18.00 |
| Legacy | 16.00 | 14.00 | 14.00 |
| Star | 18.00 | 18.00 | 17.00 |

**Weight is shown as the average weight per fruit

DETAILED DESCRIPTION OF THE NEW VARIETY

The following additional information is provided to further describe the new variety.

Variety: 'Plablue 1542'. Breeder Ref. 15.09.003

Latin name: *Vaccinium corymbosum* L.

Common name: Southern highbush blueberry

Plants are growing in containers of 45 liters of capacity.

Plant:

*Habit*.—Upright.

*Vigor*.—Weak.

*Height of plant*.—About 1.90 m.

*Canopy diameter*.—About 1.60 m.

*Twigginess*.—Medium.

*Suckering*.—Low.

*Evergreenness*.—Evergreen.

*Chilling requirement*.—Approximately 100-200 hour at temperatures at or below 7° C.

*Cold hardiness*.—Has not been grown in all environments including harsh winter environments. Cold tolerance is expected to be low.

Trunk and branches:

*Surface texture new wood*.—Smooth.

*Surface texture* 1 *year wood*.—Smooth.

*Surface texture* 2 *years and older wood*.—Rough.

*Diameter new wood*.—About 6.0 to 7.0 mm.

*Diameter* 1 *year wood*.—About 10.0 to 11.0 mm.

*Diameter* 2 *years old wood*.—About 17.5 to 19.0 mm.

*Color*.—New wood about yellow-green color (RHS Yellow-Green group color near 144C to 144 B) transitioning to about greyed-orange color (RHS Greyed-Orange group color near 177 B to 177 A) in about 2 year old wood.

Leaf:

*Internode length*.—About 16.5 to 21.5 mm.

*Leaf arrangement*.—Alternate simple.

*Length*.—About 7.5 to 8.0 cm.

*Width*.—About 4.0 to 4.5 cm.

*Leaf shape*.—Elliptic.

*Shape of tip*.—Acute.

*Shape of base*.—Obtuse.

*Shape of margin*.—Serrate.

*Venation pattern*.—Reticulate.

*Mature leaf color upperside*.—RHS Green group color near 143 B to 143 A.

*Mature leaf color underside*.—RHS Yellow-Green group color near 144 B to 144 A.

*Pubescence upper leaf surface*.—Absent.

*Pubescence under leaf surface*.—Absent.

*Pubescence leaf margin*.—Absent.

*Precocity*.—New vegetative growth before flowering.

Petiole:

*Length*.—About 3.5 to 4.5 mm.

*Width* (*diameter*).—About 1.0 to 2.0 mm.

*Texture*.—Smooth.

*Color*.—RHS Yellow-Green group color near 145 B to 145 A.

Flower:

*Flower arrangement*.—Compound raceme. Clusters at the end of branches.

*Flower shape*.—Urceolate.

*Flowers per cluster*.—About 7 to 8.

*Flower fragrance*.—Faint. Sweet.

*Immature flower color*.—RHS Red group color near 54 C to 54 B.

*Corolla*.—Length: About 9.0 to 10.0 mm. Diameter: About 7.0 to 8.0 mm. Aperture width: About 4.0 to 5.0 mm. Color: RHS White group color near 155 B to 155 A. Texture: Smooth.

*Peduncle*.—Length: About 14.0 to 14.5 mm. Color: RHS Yellow-Green group color near 144 C to 144 B.

*Pedicel*.—Length: About 12.0 to 12.5 mm. Color: RHS Yellow-Green group color near 144 C to 144 B. Calyx (with sepals) Diameter: 6.5 to 8.0 mm. Calyx texture: Smooth. Color center of calyx: RHS Yellow-Green group color near 146 D to 146 C. Color sepals: RHS Yellow-Green group color near 144 D to 144 C. Attitude of sepals: Erect. Type of sepals: Reflexed.

*Stamen*.—Length: About 4.5 to 5.0 mm. Number per flower: About 10 to 11. Filament color: RHS Yellow-Green group color near 145 D to 145 C.

*Style*.—Length: About 6.9 to 7.3 mm. Color: RHS Yellow-Green group color near 145 C to 145 B.

*Pistil*.—Length: About 8.3 to 8.7 mm. Ovary color: RHS Yellow-Green group color near 145 D to 145 C.

*Anther*.—Length: About 3.0 to 3.5 mm. Number: About 10 to 11. Color: RHS Greyed-Orange group color near 165 B to 165 A.

*Pollen*.—Abundance: Medium. Color: RHS Yellow-Orange group color near 20 C to 20 B.

*Self-compatibility*.—The cultivar has demonstrated a high degree of self-compatibility.

Fruit:

*Fruiting type*.—On one-year-old and current season's shoots.

*Calyx aperture*.—About 7.0 to 9.0 mm.
*Calyx lobes*.—About 4 to 5 lobes.
*Calyx depth*.—About 2.5 to 3.0 mm.
*Pedicel length*.—About 9.5 to 10.0 mm.
*Pedicel surface texture*.—Smooth.
*Peduncle length*.—About 10.0 to 11.0 mm.
*Peduncle surface texture*.—Smooth.
*Berries per cluster*.—About 7 to 8.
*Berry detachment*.—Easy.
*Weight*.—About 18 to 22 grs.
*Height*.—About 14.0 to 15.0 mm.
*Width*.—About 24.0 to 26.0 mm.
*Shape*.—Oblate.
*Color with wax*.—RHS Violet-Blue group color near 97 D to 97 C.
*Color with wax removed*.—RHS Black group color near 202 A.
*Wax*.—Persistent wax.
*Surface wax abundance*.—Moderate.
*Flesh color*.—RHS Yellow-Green group color near 149 D to 149 C.
*Pedicel scar*.—About 0.9 to 1.2 mm.
*Firmness*.—1.0 Kg. Firmness: It is the fruit's resistance to penetration measured in Kilograms (Kg). The measure given has been obtained by penetrometer ROZE Mod. Arbelette, with a 20 $mm^2$ section ahead.
*Texture of flesh*.—Crisp and juicy.

Seed:

*Color*.—RHS Greyed-Orange group color near 165 C to 165 B.
*Length*.—About 1.5 to 2.5 mm.
*Width*.—About 0.90 to 1.0 mm.
*Weight*.—About 0.3 to 0.4 mg.
*Seeds per berry*.—About 10 to 12.

General: The growing period in Huelva, Spain, where the observations on primocane production were made, is between about November 20 and June 22 of the following year. 'Plablue 1542' is a blueberry variety that benefits from induction to flowering by chilling, usually a few hours (approximately 100-200 hours) are sufficient, preferably at temperatures of 7° C. or less. Normally, the minimum number of hours is accumulated in the field during several days. 'Plablue 1542' is a variety with consistent fruit production beginning in on first days of February and ending at the middle of June. After planting as aforesaid, plants are grown in containers under tunnel. Water and fertilizer were applied through drip irrigation.

Date of planting: About October 15 in the farm of La Mogalla, in Cartaya (Huelva), Spain, about 7° W, 37° N, 45 feet elevation. Time of flowering data: 10% flowering about October 15. First mature fruits are about February 6 (15-20 g/plant), with a maximum production at the beginning of May.

Storage Qualities: 'Plablue 1542' fruit maintains their quality characteristics when keeping them in a frigo chamber at temperatures of about 2° C. for a duration of about 30 days. The fruit's color remains substantially the same. Shelf life of 'Plablue 1542' is good.

Use/market: The berries of 'Plablue 1542' are suitable for consumption as fresh fruit. Also, they are amenable to processing.

Disease resistance: No particular sensitivity to any disease or pest has been observed for 'Plablue 1542'

I claim:

1. A new and distinct blueberry plant of the variety substantially as shown and described.

* * * * *